United States Patent [19]
Feldman

[11] Patent Number: 5,279,589
[45] Date of Patent: Jan. 18, 1994

[54] IV BAG WITH A NECK STRAP

[76] Inventor: Maria C. Feldman, 5214 E. Vista St., Long Beach, Calif. 90803

[21] Appl. No.: 975,831

[22] Filed: Nov. 13, 1992

[51] Int. Cl.⁵ .............................................. A61M 5/00
[52] U.S. Cl. .................................. 604/262; 604/408
[58] Field of Search ............... 604/403, 408, 262, 345, 604/80, 81, 257, 258, 322, 323, 324, 325, 326, 327, 328, 329, 330, 331; 383/14, 24, 78, 22

[56] References Cited

U.S. PATENT DOCUMENTS

| | | | |
|---|---|---|---|
| 2,304,708 | 12/1942 | Ritter | 604/262 |
| 2,999,387 | 9/1961 | Andelin | 383/22 |
| 3,730,421 | 5/1973 | Stanley | 383/78 |
| 3,777,697 | 12/1973 | Woessner | 604/262 |
| 4,368,765 | 1/1983 | Laricin et al. | 604/408 |
| 5,125,920 | 6/1992 | Ishida | 604/408 |

FOREIGN PATENT DOCUMENTS

| | | | |
|---|---|---|---|
| 0006816 | of 1898 | United Kingdom | 604/403 |
| 2155021 | 9/1985 | United Kingdom | 604/403 |

Primary Examiner—C. Fred Rosenbaum
Assistant Examiner—Manuel Mendez
Attorney, Agent, or Firm—W. Edward Johansen

[57] ABSTRACT

An IV bag has a front surface layer, a rear surface layer, a top peripheral edge, a right side peripheral edge, a bottom peripheral edge and a left side peripheral edge. The front surface layer is joined to the rear surface layer along the top, right side, bottom and left side peripheral edges to form the IV bag. A neck strap is fixedly coupled to the top peripheral edge and is detachably coupled to the left side and right side peripheral edges. The neck strap, once detached, may be placed around the neck of a user to support the IV bag. The neck strap by being detachably coupled along the right side and left side periperhal edges of the IV bag functions as a neck engaging support for the IV bag. During an emergency situation it is not necessary for the user to search for the neck strap becuase the neck strap is fixedly coupled to the top periperhal edge of the IV bag.

1 Claim, 1 Drawing Sheet

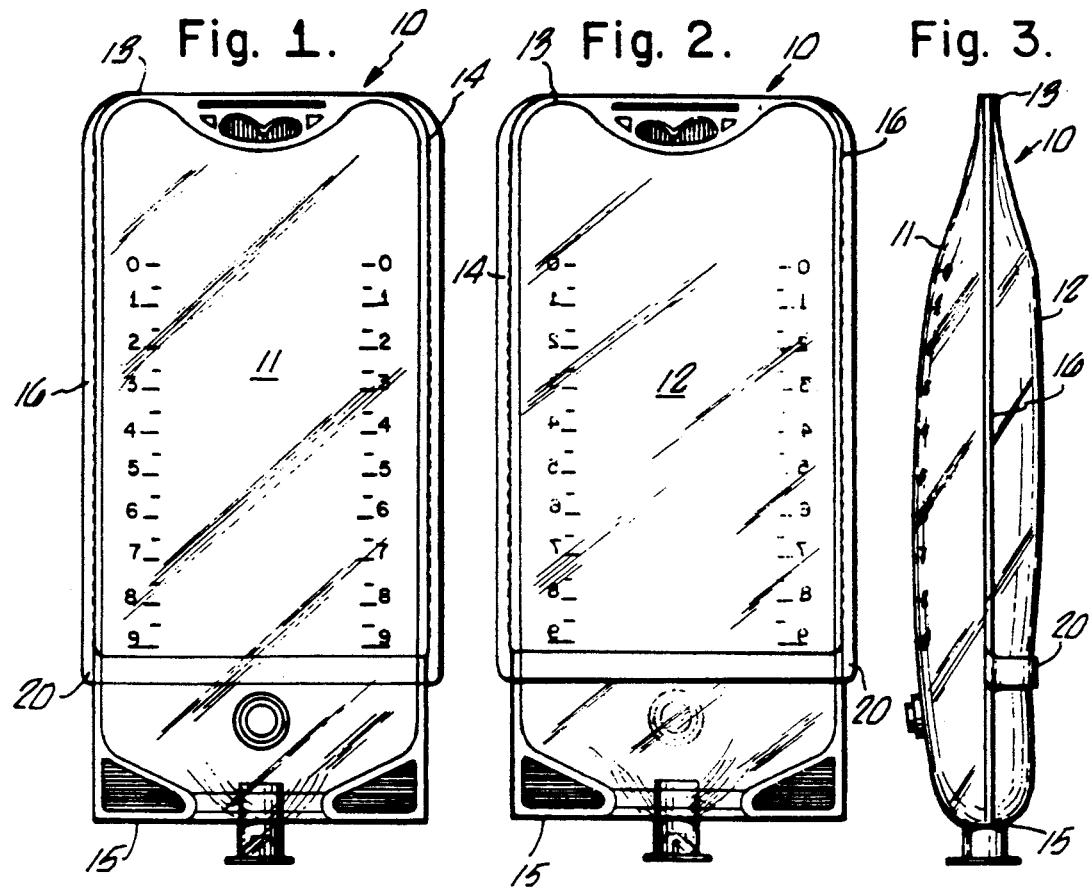
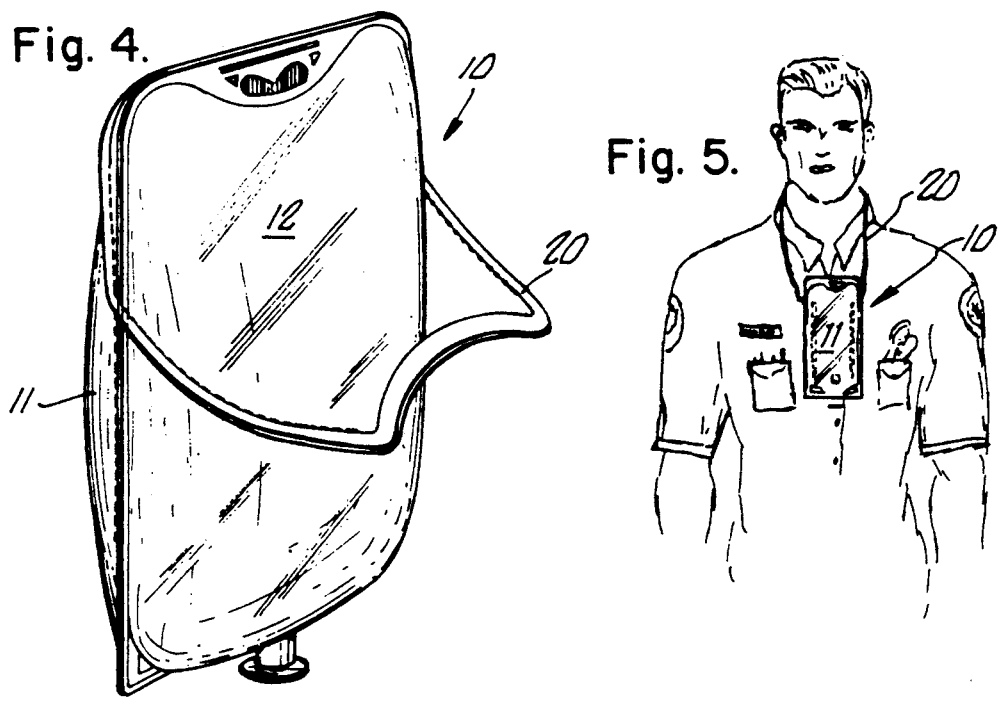

IV BAG WITH A NECK STRAP

BACKGROUND OF THE INVENTION

The field of the invention is neck engaging supports for IV bags.

U.S. Pat. No. 4,905,882 teaches a neck engaging support for a medical device which engages and is supported from the neck of a medical practitioner. A rod-like support device has a downwardly opening, generally U-shaped hook member dimensioned to fit around the neck of a user with the open area positioned in front of the chest region with one leg of the U-shaped member having a smaller hook for engagement with an IV bag in order to support the IV bag in elevated position without using the hands such as is frequently necessary during emergency situations when a patient is being conveyed on a stretcher from the site of the emergency to an ambulance or a hospital. The rod-like support enables the user of the medical device to actually carry one end of the stretcher while at the same time supporting the IV bag in an elevated position. During an emergency situation it is often necessary for the user to search for the neck engaging support because it is not fixedly coupled to the IV bag.

U.S. Pat. No. 4,511,157 teaches an apparatus which interconnects a wheelchair and portable wheeled IV stand. The apparatus maintains the wheelchair and IV stand in a fixed spaced relationship with respect to one another when the wheelchair is being pushed by a medical attendant.

U.S. Pat. No. 4,541,596 teaches a portable intravenous pole which is for use in combination with a surface on which an emergency victim is lying. The weight of the emergency victim's body supports an IV bag.

SUMMARY OF INVENTION

The present invention is generally directed to a an IV bag which has a front surface layer, a rear surface layer, a top peripheral edge, a right side peripheral edge, a bottom peripheral edge and a left side peripheral edge. The front surface layer is joined to the rear surface layer along the top, right side, bottom and left side peripheral edges to form the IV bag.

In a first aspect of the present invention, a neck strap is fixedly coupled to the top peripheral edge and is detachably coupled to the left side and right side peripheral edges. The neck strap, once detached, may be placed around the neck of a user to support the IV bag.

In a second aspect of the present invention, the neck strap by being detachably coupled along the right side and left side periperhal edges of the IV bag functions as a neck engaging support fot the IV bag.

In a third aspect of the present invention, the neck strap being fixedly coupled to the top periperhal edge of the IV bag realizes that during an emergency situation it is not necessary for the user to search for the neck strap.

Other aspects and many of the attendant advantages will be more readily appreciated as the same becomes better understood by reference to the following detailed description and considered in connection with the accompanying drawing in which like reference symbols designate like parts throughout the figures.

The features of the present invention which are believed to be novel are set forth with particularity in the appended claims.

BRIEF DESCRIPTION OF THE DRAWING

FIG. 1 is a front elevational view of an IV bag and a neck strap according to the present invention.

FIG. 2 is a rear elevational view of the IV bag of FIG. 1.

FIG. 3 is a right side elevational view of the IV bag of FIG. 1.

FIG. 4 is a perspective view of the IV bag and the neck strap of FIG. 1.

FIG. 5 is a schematic drawing of a user using the strap neck to support the IV bag of FIG. 1.

DESCRIPTION OF THE PREFERRED EMBODIMENT

Referring to FIG. 1 in conjunction with FIG. 2 and FIG. 3 an IV bag 10 has a front surface layer 11, a rear surface layer 12, a top peripheral edge 13, a right side peripheral edge 14, a bottom peripheral edge 15 and a left side peripheral edge 16. The front surface layer 11 is joined to the rear surface layer 12 along the top, right side, bottom and left side peripheral edges 13, 14, 15 and 16 to form the IV bag 10.

Referring to FIG. 4 in conjunction with FIG. 2 and FIG. 3 a neck strap 20 is fixedly coupled to the top peripheral edge 13 of the IV bag 10. The neck strap 20 is detachably coupled to the left side and right side peripheral edges 14 and 16 of the IV bag 10.

Referring to FIG. 5 in conjunction with FIG. 4 the neck strap 20, once detached, may be placed around the neck of a user to support the IV bag 10. The advantages of using the neck engaging support of U.S. Pat. No. 4,905,882 are realized by the neck strap 20 being detachably coupled along the right side and left side periperhal edges 14 and 16 of the IV bag 10. There is another advantage in that during an emergency situation it is not necessary for the user to search for the neck strap 20 because it is fixedly coupled to the top peripheral edge 13 of the IV bag 10.

From the foregoing it can be seen that an IV bag with a neck strap has been described. It should be noted that the sketches are not drawn to scale and that distance of and between the figures are not to be considered significant.

Accordingly it is intended that the foregoing disclosure and showing made in the drawing shall be considered only as an illustration of the principle of the present invention.

What is claimed is:
1. An IV bag with a neck strap comprising:
   a. an IV bag having a front surface layer, a rear surface layer, a top peripheral edge, a right side peripheral edge, a bottom peripheral edge and a left side peripheral edge, said front surface layer being joined to said rear surface layer along said top, right side, bottom and left side peripheral edges to form said IV bag; and
   b. a neck strap fixedly coupled to said top peripheral edge and detachably coupled to said left side and right side peripheral edges whereby said neck strap, once detached, may be placed around the neck of a user to support said IV bag.